United States Patent
Deguilio

(10) Patent No.: US 9,352,113 B2
(45) Date of Patent: May 31, 2016

(54) DEVICE AND METHOD FOR DETERMINING SIZING INFORMATION FOR CUSTOM MASK DESIGN OF A FACIAL MASK

(71) Applicant: KONINKLIJKE PHILIPS N.V., Eindhoven (NL)

(72) Inventor: Andrew Phillip Deguilio, Cheswick, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/384,212

(22) PCT Filed: Mar. 11, 2013

(86) PCT No.: PCT/IB2013/051901
§ 371 (c)(1),
(2) Date: Sep. 10, 2014

(87) PCT Pub. No.: WO2013/136246
PCT Pub. Date: Sep. 19, 2013

(65) Prior Publication Data
US 2015/0055140 A1    Feb. 26, 2015

Related U.S. Application Data

(60) Provisional application No. 61/610,546, filed on Mar. 14, 2012.

(51) Int. Cl.
*G01B 11/24* (2006.01)
*A61M 16/06* (2006.01)
*G01B 11/25* (2006.01)

(52) U.S. Cl.
CPC ............... *A61M 16/06* (2013.01); *G01B 11/25* (2013.01); *A61M 2016/0661* (2013.01); *A61M 2207/10* (2013.01)

(58) Field of Classification Search
CPC . A61K 31/553; A61K 31/554; A61K 9/0073; A61K 9/0075; A61K 9/0078; A61K 31/55; A61K 31/551; G01B 11/25
See application file for complete search history.

(56) References Cited

U.S. PATENT DOCUMENTS 4,434,467 A * 2/1984 Scott ............................... 700/90
5,584,125 A * 12/1996 Prete ......................... 33/501.45

(Continued)

FOREIGN PATENT DOCUMENTS

| CN | 101249293 A | 8/2008 |
| CN | 101305262 A | 11/2008 |

(Continued)

*Primary Examiner* — Michael P Stafira
(74) *Attorney, Agent, or Firm* — Michael W. Haas

(57) ABSTRACT

The present invention relates to a mask sizing device (10) for determining sizing information for custom mask design of a facial mask, wherein the mask sizing device (10) comprises an image projecting unit (20) for projecting an image (16) onto a person's face (18), wherein the image (16) comprises at least a number of contact points of the facial mask, said contact points representing potential points of contact of the facial mask with the person's face (18), a control unit (22) for controlling said image projection unit (20) to adjust dimension, position and/or orientation of the image (16) and/or to project an image including two or more sub-images having different dimensions, positions and/or orientations, a sub-image comprising at least a number of contact points of a facial mask; and a read-out unit (24) for reading out sizing information comprising information about the dimension, position and/or orientation of the image (16) and/or a selected sub-image.

15 Claims, 2 Drawing Sheets

(56) References Cited

U.S. PATENT DOCUMENTS

| | | |
|---|---|---|
| 6,728,589 B1 * | 4/2004 | Delache et al. ............... 700/117 |
| D644,729 S | 9/2011 | Ferris |
| 2006/0023228 A1 | 2/2006 | Geng |
| 2008/0060652 A1 | 3/2008 | Selvarajan |
| 2011/0162654 A1 | 7/2011 | Carroll |
| 2012/0305003 A1 * | 12/2012 | Mark ....................... 128/206.24 |

FOREIGN PATENT DOCUMENTS

| | | |
|---|---|---|
| EP | 1116492 A2 | 7/2001 |
| FR | 2928256 A1 | 9/2009 |
| WO | WO2011073813 A1 | 6/2011 |

* cited by examiner

DEVICE AND METHOD FOR DETERMINING SIZING INFORMATION FOR CUSTOM MASK DESIGN OF A FACIAL MASK

CROSS-REFERENCE TO RELATED APPLICATIONS

This patent application claims the priority benefit under 35 U.S.C. §371 of international patent application no. PCT/IB2011/051901, filed Mar. 11, 2013, which claims the priority benefit under 35 U.S.C. §119(e) of U.S. Provisional Application No. 61/610,546 filed on Mar. 14, 2012, the contents of which are herein incorporated by reference.

FIELD OF THE INVENTION

The present invention relates to a mask sizing device and a respective method for determining sizing information for custom mask design of a facial mask.

BACKGROUND OF THE INVENTION

Facial contour and geometry are being used to design masks and to identify mask usage in many medical fields including CPAP (Constant Positive Air Pressure). CPAP masks are used to provide a breathable mixture of gases, typically air, provided at above ambient pressure to a patient. A CPAP mask forms a seal around a nose and mouth of a patient's face, providing an interface between the air source and the patient's respiratory system that is ideally free of leaks. CPAP masks are used in a wide variety of medical treatment procedures including for instance the treatment of Obstructive Sleep Apnea (OSA). During such treatment, the patient wearing the mask inhales the pressurized air, which prevents tongue tissue from obstructing the air passages. Because of the use of pressurized air, the facial mask must provide a proper seal with the patient's face.

A CPAP mask typically comprises a cuff and a dome that is optionally supported by a forehead pad. The cuff forms a seal around the patient's face, whereas the dome sits over the patient's nose and mouth and provides a conduit to the source of air. Ideally, the seal is air-tight under the pressure in normal service. Typically, cuffs in CPAP masks comprise silicon gaskets, and other materials with similar properties of high elasticity.

Besides good sealing qualities, the facial mask should also feature proper fitting and comfort properties. However, CPAP masks often lead to irritations around the face of the patient. This is particularly found in medical environments, where the mask may be worn for hours or days without changing or removing from the face. This occurs because silicon gaskets often do not seal well to the patient's face, especially around the bridge and lower sides of the nose. The resulting air leaks into the patient's eyes, causing irritations. These air leaks can be avoided by pushing the CPAP mask more tightly to the patient's face. However, this pressure can lead to minor red marks or open sores. Additionally, individuals have widely varying sensitivities to mechanical pressure. A combination of skin and eye irritations reduces patient tolerance and compliance with the medical procedure utilizing the mask.

Obviously, the sizes and shapes of patient's faces differ from person to person. In order to maximize compliance for the CPAP therapy, the CPAP masks have to be customized and to be adjusted as well as possible to the patient's face. Therefore, personalized sizing information has to be captured from the patient's face for customizing the CPAP masks. Known sizing gauges are based on cut-outs in bags, plastic sliders, or templates on packaging that contacts the patient's face. However, the known sizing gauges cover a part of the patient's face and thereby obstruct the view of a clinician trying to fit the facial mask. This, in turn, will lead to an inaccurate fitting of the facial mask. Moreover, the current sizing gauges are not suitable for multi-patient use, because they need to be cleaned or disinfected after contacting the patient's face. Additionally, the known sizing gauges are extra components shipped with each mask and thereby create a lot of plastic waste. These problems also apply to other mask types or masks used for other applications, like BiPAP masks (Biphasic Positive Airway Pressure), masks for firefighters, military masks etc.

SUMMARY OF THE INVENTION

Accordingly, it is an object of the present invention to provide a mask sizing device and a respective method that overcomes the shortcomings of the conventional sizing gauges and methods.

In a first aspect of the present invention, a mask sizing device is presented that determines sizing information for custom mask design of a facial mask. The mask sizing device comprises an image projecting unit for projecting an image onto a person's face, wherein the image comprises at least a number of contact points of the facial mask, said contact points representing potential points of contact of the facial mask with the person's face, a control unit for controlling said image projection unit to adjust dimension, position and/or orientation of the image and/or and/or to project an image including two or more sub-images having different dimensions, positions and/or orientations, a sub-image comprising at least a number of contact points of a facial mask; and a read-out unit for reading out sizing information comprising information about the dimension, position and/or orientation of the image and/or a selected sub-image.

In a further aspect of the present invention, a method for determining sizing information for custom mask design of a facial mask is presented. The method comprises projecting an image onto a person's face, wherein the image comprises at least a number of contact points of the facial mask, said contact points representing potential points of contact of the facial mask with the person's face, adjusting dimension, position and/or or orientation of the image and/or projecting an image including two or more sub-images having different dimensions, positions and/or orientations, a sub-image comprising at least a number of contact points of a facial mask; and reading out sizing information comprising information about the dimension, position and/or orientation of the image and/or a selected sub-image.

When applying the device according to the present invention, an outline of at least a part of a facial mask touching a person's face during use or other markers/key-points that are characteristic of the size of a particular mask are projected onto a person's face using light. By means of the control unit and the image projecting unit, the projected image can be adjusted in order to optimally fit the projected mask outline to the person's face. The read-out unit facilitates to read out the sizing information of the adjusted image, i.e. an image selected after the adjustment.

Further, it is also possible to project an image having two or more sub-images (subsequently or simultaneously) and to select a sub-image which best fits the projected mask outline to the person's face. Each of the sub-images may thus represent the outline of a different mask, mask type or mask size. The selected sub-image may then also be further adjusted to find the optimum fit.

The mask sizing device according to the present invention will give, for example, a mask designer/manufacturer a much more accurate measure of the appropriate mask size for the person, because it does not obstruct the field of view like the known sizing gauges based on cut-outs in bags, plastic sliders etc. Since the presented sizing device does not need to be brought into contact with a person's face, it has not to be disinfected or cleaned when used for multiple persons. Furthermore, the proposed sizing device is a reusable sizing gauge that eliminates the need to ship extra components with each mask, thereby avoiding a lot of plastic waste. By applying the sizing device according to the present invention good fitting and sealing properties of the facial mask can be achieved. This, in turn, leads to a high wearing comfort and a high acceptance of the medical procedures.

Preferred embodiments of the invention are defined in the dependent claims.

In a first embodiment, the image projecting unit is configured to project an image comprising an outline of a cushion of the facial mask. The image preferably comprises an outline of a cushion, since the cushion constitutes a very critical contact part of the facial mask. The cushion has to feature high fitting qualities in order to provide good sealing capabilities and to avoid at the same time skin and eye irritations.

According to another embodiment, the image projecting unit is configured to project an image comprising an outline of a forehead pad of the facial mask. A not correctly adjusted forehead pad can lead to minor red marks or even open sores on the patient's face. Therefore, the forehead pad represents a key fitting feature of a facial mask.

In a further embodiment, the image projecting unit is configured to project an image comprising multiple color representing different sizes, different types and/or different areas of the facial mask. With this embodiment, the clinician can at the same time project different sub-images, each in a different color and each representing different sizes and/or different types of a facial mask, onto the patient's face. This, for example, allows the clinician to select the most optimal sub-image in a first step and then start the adjustment process from this selected sub-image in a second step. Further, in the first step the best fitting mask type may thus be already determined based on the projected outlines of the different masks, which is then adapted according to the sizing information obtained in the adjustment process. This embodiment also allows to directly select one of the multiple sub-images directly and use the sizing information from the selected sub-image for custom mask design.

In a further embodiment, the control unit is configured to control the image projecting unit to separately adjust point positions of the contact points and the read-out unit is configured to read out the sizing information comprising the point positions of the contact points. The separate adjustment of all the point positions of the contact points provides a very flexible modification of a mask outline and leads to good fitting capabilities of the facial mask. As a result, a facial mask can be provided that features good sealing properties.

In yet another embodiment, the control unit is configured to control the image projecting unit to modify height, width and/or angle of the image. By modifying these parameters the dimension, position and/or orientation of the image can exactly be set.

In a further embodiment, the adjustment unit comprises a user interface for manual adjustment of the dimension, position and/or orientation of the image. By means of the user interface, the clinician can manually adjust the image in order to capture the sizing information for a custom mask design or to determine the best fitting mask out of a range of given masks.

In another embodiment, the mask sizing device further comprises a capturing unit for capturing a sizing image comprising the person's face and the image projected onto the person's face. A possible embodiment of said capturing unit could be, for example, a video device that records the projected image on the person's face. In this embodiment, for example, a zoom functionality can be applied to the sizing image to more precisely analyze the image projected onto the person's face. This provides the possibility to improve the fitting of the facial mask.

In a further embodiment, the control unit is configured to control the image projecting unit to automatically adjust the dimension, position and/or orientation of the image based on the sizing image. The automatic adjustment could, for example, be done on the basis of the captured sizing image that is analysed by a computer program in order to find the best fit of the mask. After the analysis of the sizing image respective setting commands are sent to the control unit. This process significantly eases the work of the clinician trying to find the best fitting outline of a cushion of the facial mask. As an option, the image can first be automatically adjusted. After that is done, the outline of the cushion can manually be modified to achieve the best fit.

According to another embodiment of the present invention, the read-out unit comprises optical read-out means for providing an optical representation of the sizing information. The optical representation can, for example, be an image of an adjusted outline of a cushion and/or forehead pad of the facial mask that is read out by a camera or an image sensor.

In a further embodiment, the read-out unit comprises electrical read-out means for providing electrical values representing the sizing information. The electrical values can be voltages and/or electrical current values that represent the settings of the adjustment unit after the image has been adjusted to the person's face.

According to another embodiment of the present invention, the read-out unit is coupleable to a computer system for providing the sizing information to the computer system. The sizing information can be stored in a computer system in a patient's record for a future reference. Based on the sizing information, the computer system could make recommendations for mask sizing, specific masks or type of masks for a person. The sizing information can also be sent to a system to manufacture a custom cushion.

According to another embodiment of the present invention, the mask sizing device further comprises a memory for storing the sizing information in a patient's record. In this embodiment, the sizing information is locally stored on the sizing device. This can be done in addition or alternatively to the storage on a computer system.

In another embodiment, the mask sizing device further comprises a processing unit configured to determine a best fitting facial mask from a range of given facial masks based on the sizing information or to determine a customized design of the facial mask. In this embodiment, the processing unit evaluates the adjusted image and compares the adjusted image with a number of predefined mask profiles. The closest match provides the best fitting facial mask.

Even if some embodiments have been described in respect to masks used in medical treatments, it shall be understood that the sizing device according to the present invention can generally be used for determining the sizing information of all kinds of facial masks used in any applications.

It also shall be understood that the claimed method has similar and/or identical preferred embodiments as the claimed device and as defined in the dependent claims.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
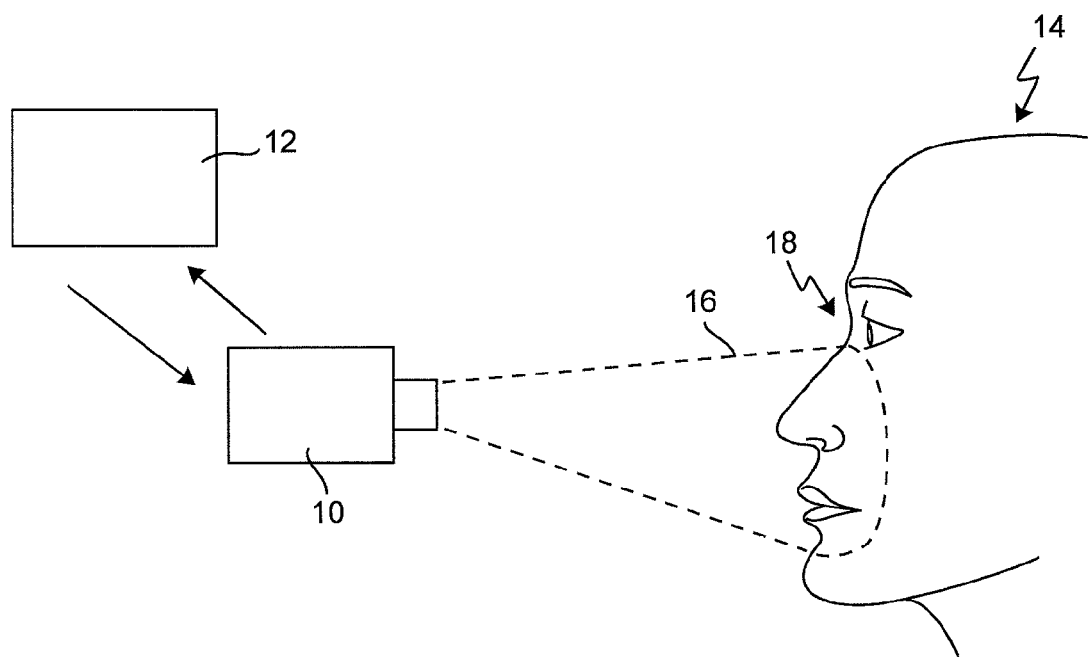
FIG. 1 shows a preferred embodiment of the proposed mask sizing device for determining sizing information for custom mask design of a facial mask.

FIG. 1 illustrates a mask sizing device 10 for determining sizing information for custom mask design of a facial mask. The mask sizing device 10 is electrically coupled to a computer system 12. The mask sizing device 10 can be used in sleep labs, hospitals or by other health care providers in order to identify the optimal mask type and/or mask size. Since the mask sizing device 10 is ideally a portable device, it can basically be used at any location. For application of the mask sizing device 10 a person 14 stands in front of the mask sizing device 10. Alternatively, the person 14 can also lie down in a sleeping position. A clinician is then projecting an image 16 onto a person's face 18 by using the mask sizing device 10. The projected image 16 comprises at least a plurality of contact points of the facial mask. The contact points represent potential points of contact of the facial mask with the person's face 18. In particular, the image 16 can comprise an outline of a cushion or a forehead pad of the facial mask. Furthermore, the projected image 16 can in general comprise all contact points of the facial mask, which affect the wearing comfort of the facial mask on the person's face 18. In addition to that, the projected image 16 can also comprise multiple colours, wherein each colour represents a different size or different type of the facial mask. The different colours can also identify different trouble areas (e.g. region of the bridge or chin) of the facial mask for sizing and fitting.

The mask sizing device 10 offers also the possibility to adjust the dimension, position and/or orientation of the image 16. In particular, it is possible to modify in real time a height, width or angle of the projected image 16 in order to identify an optimal geometry for the facial mask. In an optional configuration of the mask sizing device 10, it is also possible to separately adjust the point positions of all contact points of the facial mask. This provides an even more flexible solution for determining the best fitting facial mask contour. As soon as the optimal facial mask geometry is found, the data regarding the height, width and/or angle of the image 16, respectively the point positions of the contact points, are transferred to the computer system 12 and stored in a person's record for a future reference. Based on the person's record, the computer system 12 could also make recommendations for mask sizing, specific masks or mask types for the person 14. The data can also been sent to a manufacturing system in order to manufacture a custom facial mask or modify a standard facial mask.

By using the mask sizing device 10, a very accurate fitting of the facial masks can be achieved, since there are no cutouts, plastic sliders or templates that obstruct the view of the clinician trying to fit the facial mask. Moreover, the mask sizing device 10 can be applied to multiple persons 14 without the need for cleaning or disinfection, since there is no direct contact between the mask sizing device 10 and the person's face 18. Excess waste is avoided, because no extra components have to be shipped with each mask for fitting purposes.

The described facial masks can be applied in CPAP (Constant Positive Air Pressure) and, for example, BiPAP (Biphasic Positive Airway Pressure) therapies, i.e. in different kinds of patient interfaces. However, the usage of the facial masks is not limited to these medical treatments. The facial masks can also be used in other applications, like for example masks for fire fighters, military applications or masks used for anaesthesia.

Figure 2:
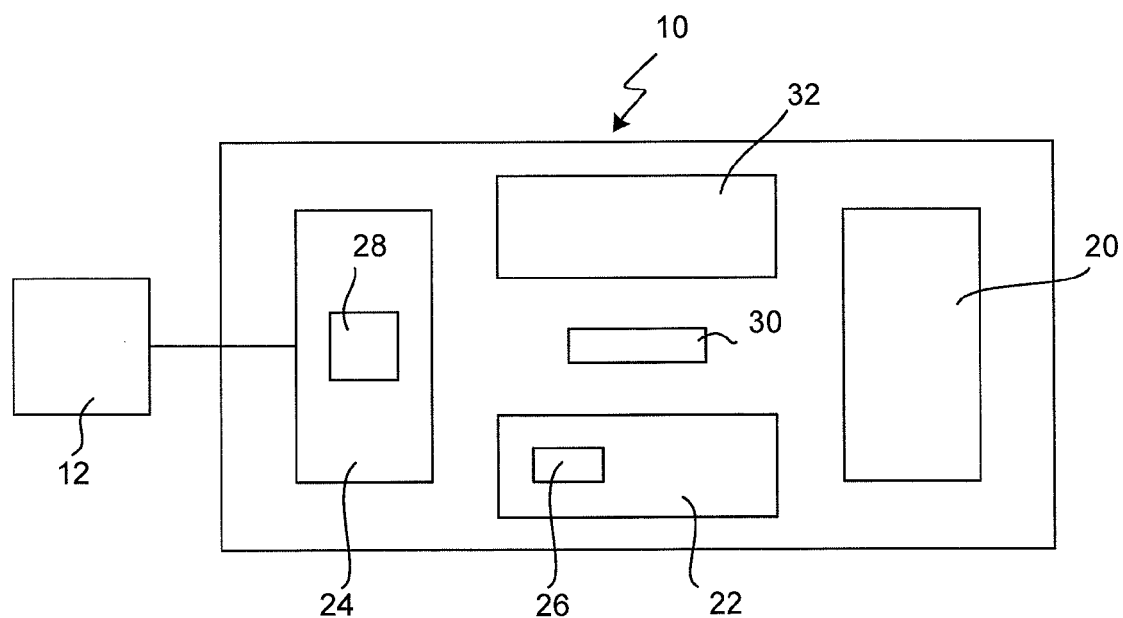
FIG. 2 shows a more detailed schematic view of the proposed mask sizing device.

FIG. 2 provides a more detailed view of an embodiment of the proposed mask sizing device 10, which is electrically connected to the computer system 12. The mask sizing device 10 comprises an image projecting unit 20 for projecting the image 16 onto the person's face 18. In addition to that, the mask sizing device 10 comprises a control unit 22 for controlling said image projection unit to adjust dimension, position and/or orientation of the image 16 and/or to project an image having two or more sub-images having different dimensions, positions and/or orientations and a read-out unit 24 for reading out sizing information comprising the information about the adjusted dimension, position and/or orientation of the image 16 and/or one of the sub-images. The control unit 22, in turn, comprises a user interface 26 for a manual adjustment of the dimension, position and/or orientation of the image 16. The read-out unit 24 comprises electrical read-out means 28 for providing electrical values representing the sizing information. Furthermore, the sizing device 10 comprises a memory 30 for storing the sizing information and a processing unit 32.

In order to determine the sizing information for the facial mask, the image projecting unit 20 is projecting light, respectively the image 16 onto the person's face 18. The image 16 typically comprises a cushion outline, a forehead pad outline or other key mask landmarks. The light projected onto the person's face 18 can comprise multiple colours representing different sizes or types of facial masks.

For example, a clinician can then operate the user interface 26 of the control unit 22 to adjust the projected cushion outline to the person's face 18. In particular, the clinician can modify the height, width and/or angle of the image 16. In addition to that, the clinician can also separately adjust the positions of all contact points, wherein the contact points represent potential points of contact of the facial mask with the person's face 18 (for example cushion outlines).

The electrical read-out means 28 of the read-out unit 24 read the sizing information from the control unit 22, wherein the sizing information comprises information about the adjusted height, width and/or angle of the image 16 and the adjusted point positions of the contact points. The electrical read-out means 28 make the sizing information available as digital information or electrical values, like voltages or electrical currents. Furthermore, the electrical read-out means 28 forward the sizing information to the computer system 12 and/or store the sizing information on the local memory 30 in a person's record.

In an alternative embodiment, the read-out unit 24 can comprise optical read-out means, which provide an optical representation of the sizing information, like a 3D-image of the best fitting mask on a screen. The optical read-out means may, for instance, comprise a camera that records an image of the image projected on the person's face. This recorded image can then be evaluated to retrieve the sizing information from it. Alternatively, the optical read-out means (e.g. a camera or other optical measurement equipment) may directly be able to determine the sizing information from the image projected onto the person's face.

Based on the stored sizing information, the processing unit 32 can determine a best fitting facial mask from a range of given facial masks. Alternatively, this functionality can also be provided by the computer system 12. Moreover, it is also possible to provide the sizing information to a manufacturing system that manufactures a custom made facial mask.

Figure 3:
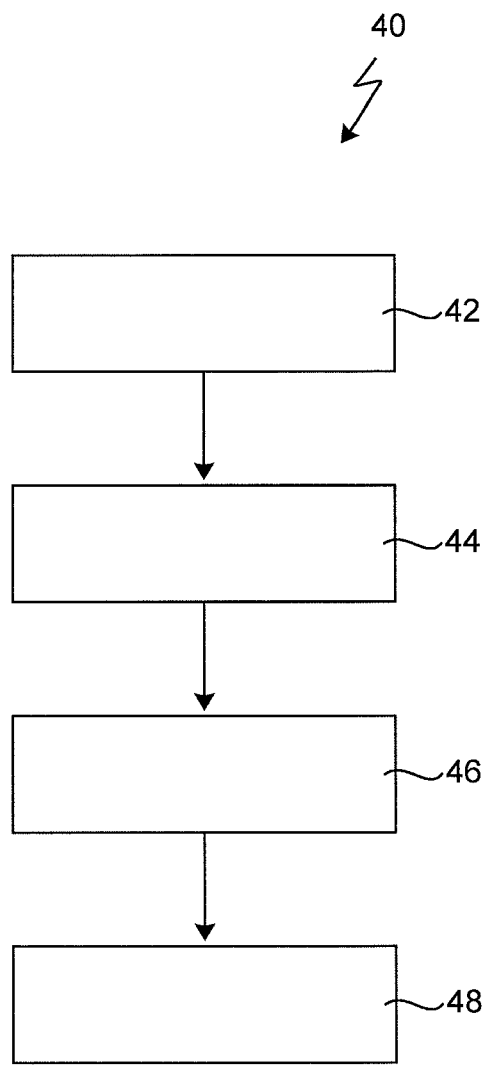
FIG. 3 shows a flow diagram illustrating the proposed method for determining sizing information for custom mask design of a facial mask.

FIG. 3 shows a flow diagram illustrating an embodiment of the proposed method 40 for determining sizing information for custom mask design of a facial mask. In a first step 42, the image 16 is projected onto the person's face 18. The image 16 comprises at least a number of contact points of the facial mask, wherein the contact points represent potential points of contact of the facial mask with the person's face 18.

In a further step 44 the dimension, position and/or orientation of the image 16 comprising, for example, a cushion outline is modified in order to adjust the cushion outline to the specific face geometry of the person 14. In this embodiment, the adjustment of the image 16 is carried out automatically by applying an additional capturing unit that is comprised by the mask sizing device 10. The capturing unit captures a sizing image comprising the person's face 18 and the image 16 projected onto the person's face 18. The capturing unit is configured to analyse the position of the image 16 on the person's face 18 and to provide new settings to the control unit 22 based on the analysis. The control unit 22, in turn, modifies the height, width and/or angle of the image 16 based on the received settings. Then again, the capturing unit can analyse the new sizing image. The approach of automatically adjusting the image 16 to the person's face 18 eases the work of a clinician.

After the image 16 has been automatically adjusted to the person's face 18, the clinician can check the achieved results. If the clinician detects a room for improvement, he can in a further step 46 manually adjust the dimension, position and/or orientation of the image 16 by using the user interface 26.

In a step 48, the sizing information comprising information about the adjusted dimension, position and/or orientation of the image 16 is read out. The sizing information is then provided to the local processing unit 32 and/or to the computer system 12. On the basis of the sizing information, the best fitting mask can be picked from an existing range of masks or the sizing information can be used to manufacture a custom made facial mask.

In an alternative embodiment an image including two or more sub-images having different dimensions, positions and/or orientations and/or representing different sizes, different types and/or different areas of the facial mask may be—simultaneously or subsequently—be projected. A sub-image that best fits the user's face may then be selected, and the sizing information may be obtained for the selected sub-image. Alternatively, the selected sub-image may be further adjusted as explained above.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A mask sizing device for determining sizing information for custom mask design of a facial mask, comprising:
    an image projecting unit for projecting an image onto a person's face, wherein the image comprises at least a number of contact points of the facial mask, said contact points representing potential points of contact of the facial mask with the person's face;
    a control unit for controlling said image projection unit to adjust dimension, position and/or orientation of the image and/or to include two or more sub-images in the image, each sub-image having different dimensions, positions and/or orientations; and
    a read-out unit for reading out sizing information comprising information about the dimension, position and/or orientation of the image and/or a selected sub-image, and wherein the image includes an outline of a cushion of the facial mask or an outline of forehead pad of the facial mask.

2. The mask sizing device according to claim 1, wherein the image includes the outline of the cushion of the facial mask.

3. The mask sizing device according to claim 1, wherein the image includes the outline of the forehead pad of the facial mask.

4. The mask sizing device according to claim 1, wherein the image includes multiple colors representing different sizes, different types and/or different areas of the facial mask.

5. The mask sizing device according to claim 1, wherein the control unit is configured to control the image projecting unit to separately adjust point positions of the contact points and wherein the read-out unit is configured to read out the sizing information comprising the point positions of the contact points.

6. The mask sizing device according to claim 1, wherein the control unit is configured to control the image projecting unit to modify height, width and/or angle of the image.

7. The mask sizing device according to claim 1, wherein the control unit comprises a user interface for manual adjustment of the dimension, position and/or orientation of the image.

8. The mask sizing device according to claim 1, further comprising a capturing unit for capturing a sizing image comprising the person's face and the image projected onto the person's face.

9. The mask sizing device according to claim 8, wherein the control unit is configured to control the image projecting unit to automatically adjust the dimension, position and/or orientation of the image based on the sizing image.

10. The mask sizing device according to claim 1, wherein the read-out unit comprises optical read-out means for providing an optical representation of the sizing information.

11. The mask sizing device according to claim 1, wherein the read-out unit comprises electrical read-out means for providing electrical values representing the sizing information.

12. The mask sizing device according to claim 1, wherein the read-out unit is coupleable to a computer system for providing the sizing information to the computer system.

13. The mask sizing device according to claim 1, further comprising a memory for storing the sizing information in a patient's record.

14. The mask sizing device according to claim 1, further comprising a processing unit configured to determine a best fitting facial mask from a range of given facial masks based on the sizing information.

15. A method for determining sizing information for custom mask design of a facial mask, comprising:
projecting an image onto a person's face, wherein the image comprises at least a number of contact points of the facial mask, said contact points representing potential points of contact of the facial mask with the person's face;
adjusting dimension, position and/or orientation of the image and/or including two or more sub-images in the image, each sub-image having different dimensions, positions and/or orientations; and
reading out sizing information comprising information about the dimension, position and/or orientation of the image and/or a selected sub-image,
wherein the image includes an outline of a cushion of the facial mask or an outline of a forehead pad of the facial mask.

* * * * *